Figure 1:
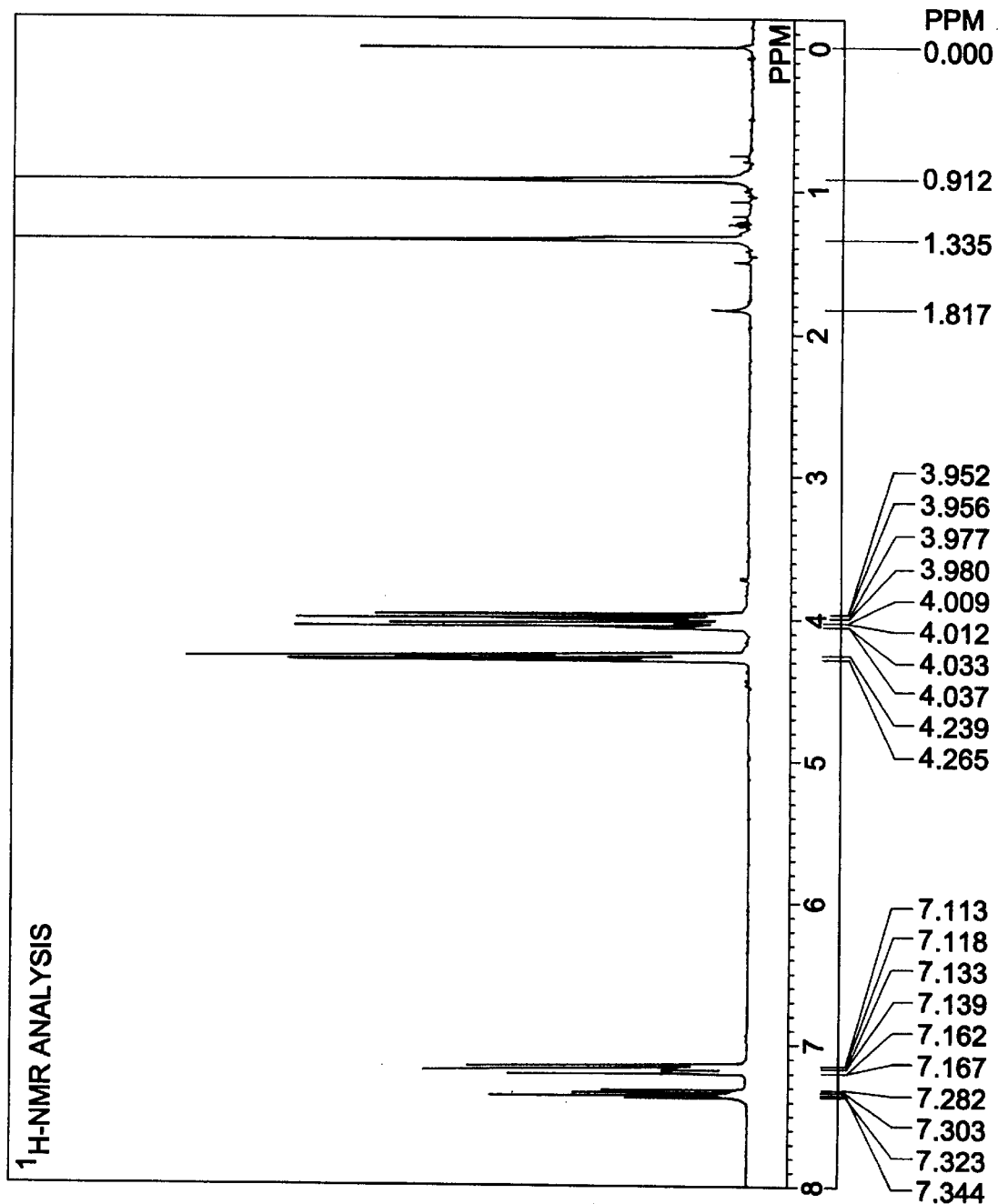

United States Patent
Staendeke

Patent Number: 5,852,197
Date of Patent: Dec. 22, 1998

[54] CYCLIC DISPHOSPHORIC ESTERS, A PROCESS FOR THEIR PREPARATION AND THEIR USE

[75] Inventor: Horst Staendeke, Lohmar, Germany

[73] Assignee: Hoechst Aktiengellschaft, Frankfurt, Germany

[21] Appl. No.: 680,133

[22] Filed: Jul. 15, 1996

[30] Foreign Application Priority Data

Jul. 17, 1995 [DE] Germany ............... 195 25 950.5

[51] Int. Cl.⁶ .................................. C07F 9/6574
[52] U.S. Cl. ............................. 558/79; 524/117
[58] Field of Search .......................... 558/79

[56] References Cited

U.S. PATENT DOCUMENTS

| | | | |
|---|---|---|---|
| 2,859,086 | 11/1958 | Feild et al. ................. | 558/79 X |
| 2,952,701 | 9/1960 | McConnell et al. ........ | 558/79 X |
| 2,974,158 | 3/1961 | Lanham ..................... | 558/79 |
| 3,965,220 | 6/1976 | Schumacher ............... | 558/101 |
| 3,970,635 | 7/1976 | Lawton et al. ............. | 558/79 X |
| 4,388,431 | 6/1983 | Mauric et al. ............. | 524/119 |
| 4,458,431 | 7/1984 | Mauric et al. ............. | 524/119 |
| 5,401,788 | 3/1995 | Tokuyasu et al. .......... | 558/79 X |

FOREIGN PATENT DOCUMENTS

| | | |
|---|---|---|
| 0 617 042 | 9/1994 | European Pat. Off. . |
| 961 354 | 4/1957 | Germany . |
| 54 080 355 | 12/1977 | Japan . |
| 80/01697 | 8/1980 | WIPO . |

*Primary Examiner*—Michael G. Ambrose
*Attorney, Agent, or Firm*—Connolly and Hutz

[57] ABSTRACT

The invention relates to cyclic diphosphoric esters of the formula

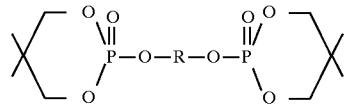

with R=methylethylene, 1,3-cyclohexylene, 1,4-cyclohexylene or 1,3-phenylene, a process for their preparation and their use as flame retardants.

2 Claims, 2 Drawing Sheets

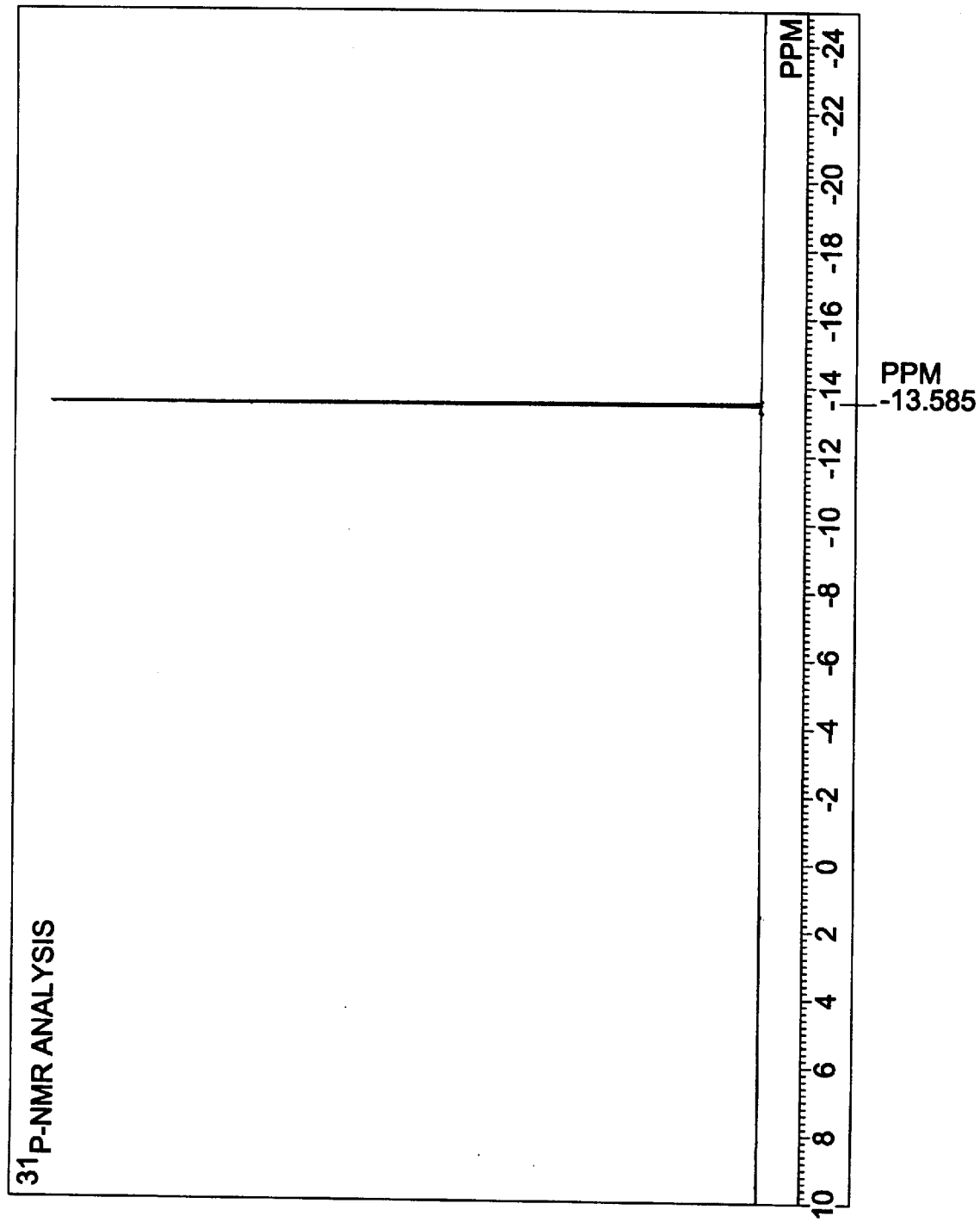

CYCLIC DISPHOSPHORIC ESTERS, A PROCESS FOR THEIR PREPARATION AND THEIR USE

Some cyclic diphosphoric esters are known from the prior art. Thus, JP-A 54 080 355 describes a cyclic disphosphoric ester of the formula

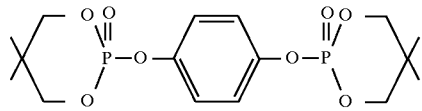

in which the phosphorus-containing groups are bound in the 1,4 position to the benzene molecule.

Surprisingly, a series of novel cyclic diphosphoric esters have now been able to be synthesized and analytically characterized.

The present invention therefore relates to novel cyclic diphosphoric esters of the formula

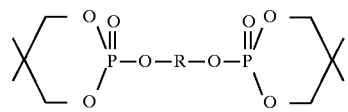

with R=methylethylene, 1,3-cyclohexylene, 1,4-cyclohexylene or 1,3-phenylene.

The invention likewise relates to a process for preparing the abovementioned cyclic diphosphoric esters, in which, in a 1st reaction step, diols are reacted with phosphorus oxychloride to give the tetrachloride of the diphosphoric ester:

The tetrachloride (I) is then reacted with 2,2-dimethyl-1,3-propanediol in a 2nd reaction step at elevated temperature, the cyclic diphosphoric ester (II) being formed with elimination of hydrogen chloride:

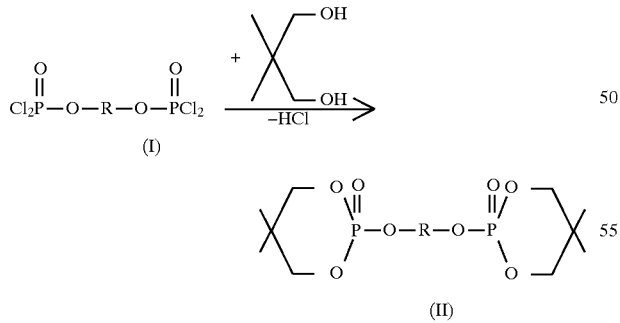

The reactions can be carried out in suitable inert solvents, such as aromatics, aliphatics, cycloaliphatics or chloroaliphatics, and in the presence of suitable tertiary amines, such as triethylamine or pyridine, and in the presence of suitable catalysts, such as aluminum chloride.

The reactions can be carried out at atmospheric pressure or under reduced pressure.

The invention further relates to the use of the cyclic diphosphoric esters of the invention as flame retardants.

EXAMPLE 1

In a first reaction step, 110 g of 1,3-dihydroxybenzene (resorcinol) were reacted with 461 g of phosphorus oxychloride [in accordance with DE-OS 22 00 137, Example 8] to give the tetrachloride of the resorcinol diphosphate. The crude product obtained was purified by vacuum distillation.

For the next reaction step, 172 g (1 mol) of this product were then dissolved in 500 ml of xylene in a stirred reactor, 104 g (1 mol) of 2,2-dimethyl-1,3-propanediol and 1.5 g of aluminum chloride (anhydrous) were added and brought to reaction in the course of 5 hours with stirring in the temperature range of 20°–120° C. After cooling to room temperature, the coarsely crystalline solids were filtered off, washed with toluene and then recrystallized from ethanol/water. 184 g of a colorless, crystalline product having the melting point 161°–163° C. were obtained, the elemental analysis of which gave the following values:

Carbon: 46.6% (theoretical for $C_{16}H_{24}O_8P_2$: 47.3%)

Hydrogen: 6.0% (theoretical for $C_{16}H_{24}O_8P_2$: 6.0%)

Phosphorus: 15.2% (theoretical for $C_{16}H_{24}O_8P_2$: 15.2%)

According to the above analytical values and the $^1$H-NMR analysis (FIG. 1) and the $^{31}$P-NMR analysis (FIG. 2), the product is 1,3-bis[2-oxo-5,5-dimethyl-1,3,2-dioxaphos-phorinanyl-2-oxy]benzene.

We claim:

1. A cyclic diphosphoric ester of the formula

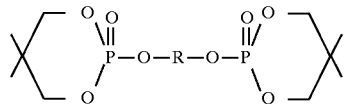

with R=1,3-phenylene.

2. A cyclic disphosphoric ester of the formula

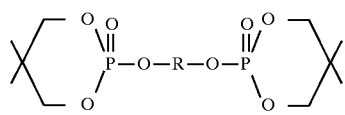

with R=1,3-cyclohexylene or 1,4-cyclohexylene.

* * * * *